United States Patent [19]

Waynant

[11] Patent Number: 5,327,446
[45] Date of Patent: Jul. 5, 1994

[54] METHOD OF EXCITING LASER ACTION AND DELIVERING LASER ENERGY FOR MEDICAL AND SCIENTIFIC APPLICATIONS

[75] Inventor: Ronald W. Waynant, Laurel, Md.

[73] Assignee: The United States of America as represented by the Secretary of the Department of Health and Human Services, Washington, D.C.

[21] Appl. No.: 38,198

[22] Filed: Mar. 26, 1993

[51] Int. Cl.$^5$ .............................................. H01S 3/03
[52] U.S. Cl. ...................................... 372/61; 372/92; 372/64; 372/87
[58] Field of Search ................ 372/61, 92, 64, 88, 372/87, 82

[56] References Cited

U.S. PATENT DOCUMENTS

| | | |
|---|---|---|
| 3,611,179 | 10/1971 | Fyler et al. . |
| 4,381,564 | 6/1983 | Newman .............................. 372/64 |
| 4,509,175 | 4/1985 | Dayl et al. . |
| 4,513,434 | 4/1985 | Waynant et al. . |
| 4,547,883 | 10/1985 | Cohn et al. ........................... 372/86 |
| 4,551,843 | 11/1985 | Ouhayoun et al. . |
| 4,593,397 | 6/1986 | Proud et al. ........................... 372/92 |
| 4,625,317 | 11/1986 | Kolb et al. ............................. 372/88 |
| 4,730,333 | 3/1988 | Butenuth ............................... 372/87 |
| 4,780,881 | 10/1988 | Zhang et al. . |
| 4,800,567 | 1/1989 | Karube ................................. 372/88 |
| 4,825,445 | 4/1989 | Koop et al. . |
| 4,847,852 | 7/1989 | Yatsiv et al. . |
| 4,891,819 | 1/1990 | Sutter, Jr. et al. . |
| 5,007,064 | 4/1991 | Seddon . |
| 5,099,492 | 3/1992 | Zajdman et al. . |
| 5,150,375 | 9/1992 | Tabata et al. ......................... 372/88 |

Primary Examiner—Léon Scott, Jr.
Attorney, Agent, or Firm—Lower, Price, LeBlanc & Becker

[57] ABSTRACT

A laser energy excitation and delivery device which includes a coaxial system of tubes having an annular space therebetween. A lasing or pumping gas is provided in the annular space and subjected to radio frequency discharge which results in the generation of laser radiation. The resulting laser radiation is propagated through and delivered from a section of the device which includes an extension of the innermost tube or an extension of each of the tubes. One embodiment of the device includes a central passageway though which various materials, including a guide wire, can pass. The device has particular utility for medical and surgical procedures.

20 Claims, 4 Drawing Sheets

5,327,446

METHOD OF EXCITING LASER ACTION AND DELIVERING LASER ENERGY FOR MEDICAL AND SCIENTIFIC APPLICATIONS

TECHNICAL FIELD

The present invention relates to rf pumped lasers. More particularly, the present invention relates to new designs of laser excitation and delivery systems and uses thereof.

BACKGROUND ART

Previous work by others has disclosed the utility of far infrared $CO_2$ lasers for medical and many other applications and the utility of short wavelength lasers for corneal ablation and other applications where UV/VUV photochemistry is helpful. Both the excitation of these lasers and the delivery of the radiation is, at best, difficult.

Excitation of $CO_2$ is most easily accomplished by gas discharge. Compact rf discharge devices which operate in this manner have been produced. However, these discharges produce radiation beams that are usually delivered by bulky articulated arms containing complex mirror systems. These devices are generally large and their size alone renders them difficult to use. At short wavelengths excitation becomes even more difficult and requires short, intense pump pulses to excite excimer lasers.

Efficient rf pumping can reduce the size of modest power UV/VUV lasers, but coupling and delivery are still difficult problems. In both the IR and UV/VUV cases, the coupling of either far infrared into some form of delivery arm or fiber, or the coupling of short wavelength laser radiation into a fiber has heretofore been unacceptable.

There presently exists a need for a compact device which produces laser excitation by rf pumping and which further provides convenient propagation and delivery of the resulting laser radiation.

DISCLOSURE OF THE INVENTION

It is accordingly one object of the present invention to provide a laser excitation and delivery system.

Another object of the present invention is to provide a compact laser excitation and delivery system which utilizes a plurality of coaxial tubes.

A further object of the present invention is to provide a compact laser excitation and delivery system which utilizes rf pumping in conjunction with a plurality of coaxial tubes.

It is a still further object of the present invention to provide a compact laser excitation and delivery system which can be used in medical or surgical procedures.

A still further object of the present invention is to provide a compact laser excitation and delivery system which allows guidance, viewing and evacuation devices to be used in conjunction with laser energy.

According to these and further objects of the present invention which will become apparent as the description thereof proceeds, the present invention provides a laser delivery device comprising an excitation section and a radiation propagation and delivery section, wherein the excitation section includes:

an inner tube;

an outer tube surrounding the inner tube and being coaxial therewith;

an annular space defined between the inner and outer tubes and containing a gas; and means to apply a radio frequency discharge to the gas in the annular space; and the radiation propagation and delivery section includes an extension of the inner tube which extends beyond the excitation section.

The present invention further provides a method of delivering laser radiation to a target area which involves:

providing concentric inner and outer tubes having an annular space defined therebetween which annular space contains a gas;

applying a radio frequency discharge to the gas in the annular space to generate laser radiation; and using at least a portion of the inner tube to propagate and deliver the laser radiation from an end thereof to a target area.

BRIEF DESCRIPTION OF DRAWINGS

The invention will be described with reference to the attached drawings which are given by way of non-limiting examples only, in which.

BEST MODE FOR CARRYING OUT THE INVENTION

Figure 1:
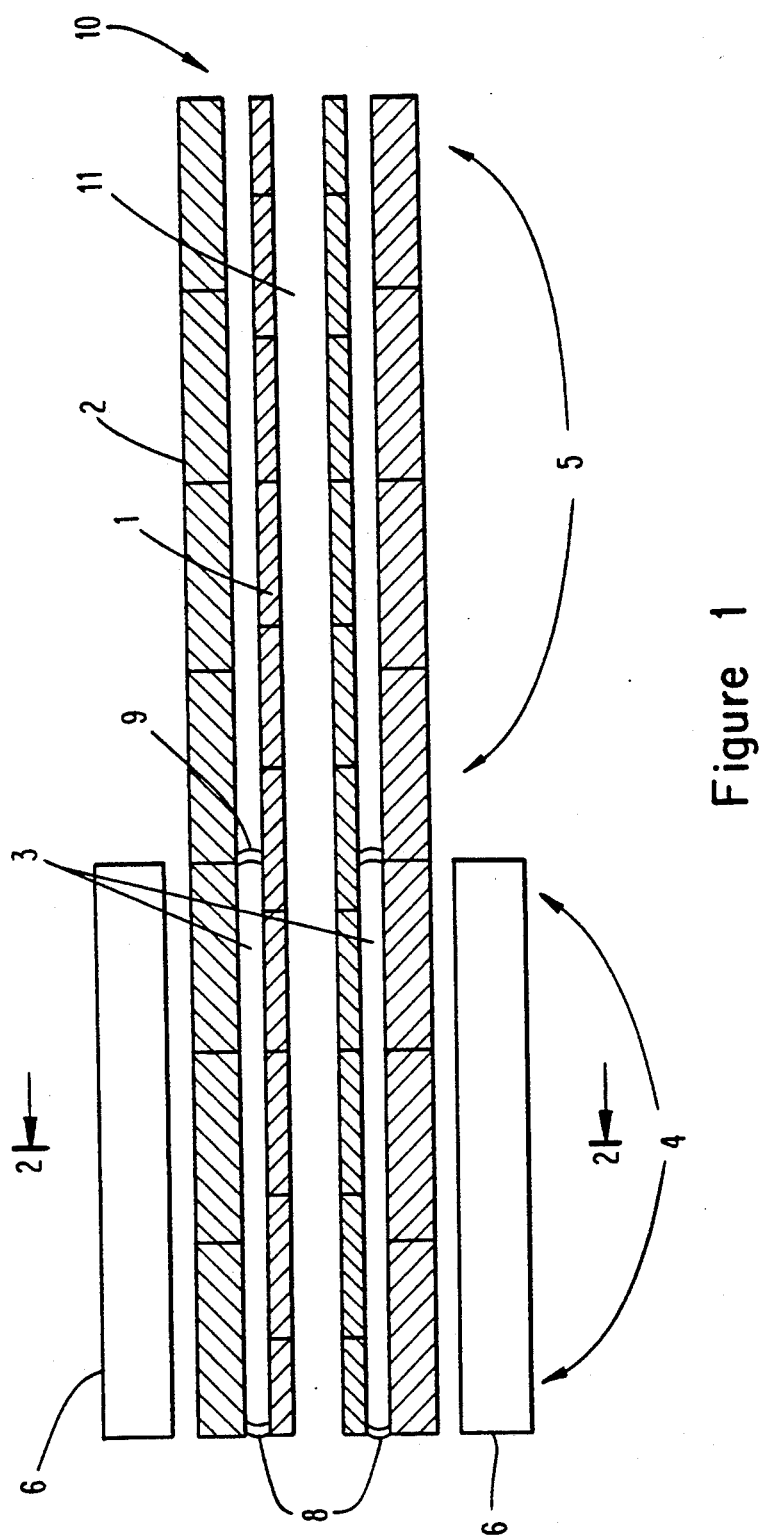
FIG. 1 is a schematic diagram of a cross sectional view of a laser delivery device according to one embodiment of the present invention.

The present invention involves rf excitation of gases contained by small solid and/or hollow fibers or tubes. The strong emissions seen near the surface in rf discharges, although poor for conventional lasers which require an axial concentration of excitation, has been discovered by applicant to be ideal for the novel coaxial systems of the present invention.

For gas lasers such as $CO_2$, coaxial hollow fibers used according to the present invention allow for excitation and propagation of radiation in the same geometric arrangement. Moreover, no coupling to additional fibers is required to deliver the radiation to a target or remote sites.

As discussed in detail below, in the present invention radiation energy is produced in one end of the coaxial fiber system and is delivered through an extension of the same fiber optics. This coaxial delivery system is ideal for surgery within the walls of many body lumens. Moreover, surgery on or near the walls of arteries, bile ducts, ureteral tubes, bowels or esophageal tubes can also be easily performed using the device of the present invention. In addition, according to one embodiment of the present invention discussed below, an open central passageway is provided in the center of the delivery system which allows for the passage of guide wires or viewing fibers, the evacuation of debris or fluids from the target area, or the introduction of gases or fluids into the target area.

The present invention allows for the use of various known pump gases for exciting the fiber lasers, including for example, $F_2$, $H_2$, Xe and Kr. In addition, various known materials can be used to construct the fiber or tube elements such as $LaF_3$, and $Al_2O_3$. The potential for pumping more that one fiber laser with the same rf generator and coupling the emissions into a common delivery fiber is also possible according to one embodiment of the present invention.

The present invention involves an excitation region which is provided by an rf source connected to a wave guide, or a pair of electrodes between which an electric field can be provided, or a chamber in which an electric field can be provided. A coaxial set of hollow fibers or tubes or a combination of hollow and solid fibers or tubes is introduced into this excitation region.

A pumping or lasing gas is introduced into an annular space between the outermost fiber or tube and the next innermost fiber or tube. A rf discharge which is produced in the excitation region or section will excite this coaxial discharge very efficiently. An appropriate resonator means is provided in the excitation region or section. According to one embodiment the resonator includes small opposed mirrors provided in the annular space between the outermost fiber or tube and the next innermost fiber or tube. In another embodiment the resonator means includes reflective coatings placed on the ends of the active fiber or tube element. Another embodiment would allow adjustable (alignable) mirror assemblies to be used as in conventional lasers.

According to one embodiment, once lasing occurs $CO_2$ emission propagates between the outermost fiber or tube and the next innermost fiber or tube and can be directed inside a subject's body toward any appropriate target. According to another embodiment in which a solid fiber or tube is coaxially pumped to lase, an extension of the solid fiber or tube is provided and used to deliver the radiation to an appropriate target.

FIG. 1 is a schematic diagram of a cross sectional view of a laser delivery device according to one embodiment of the present invention. The laser delivery device of FIG. 1 is made from two hollow coaxial tubes, including an inner tube 1 and an outer tube 2. An annular space 3 is defined between the inner tube 1 and the outer tube 2. As discussed hereafter, in this embodiment, both lasing, radiation transport and delivery are conducted in the annular space 3.

As depicted in FIG. 1, the inner and outer tubes 1 and 2 are substantially coextensive in length. An excitation section 4 is provided at one end of the coaxial tubes in which lasing occurs. The remaining portion of the laser delivery device is a radiation propagation and delivery section 5.

Figure 2:
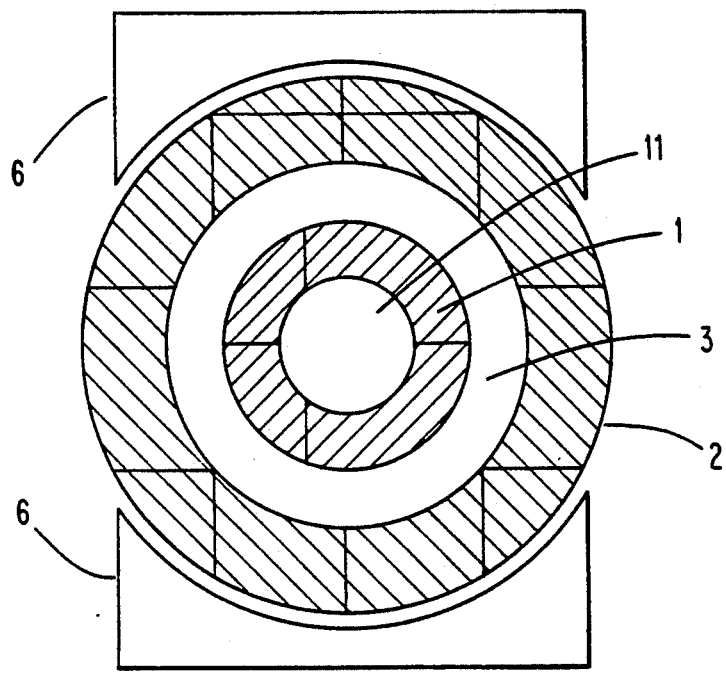
FIG. 2 is a schematic diagram of a cross sectional view of the laser delivery device of FIG. 1 taken along line II—II.

The excitation section 4 includes opposed electrodes 6 which have arcuate inner surfaces 7 (FIG. 2). The electrodes 6 are coaxial with the inner and outer tubes 1 and 2 and are positioned in close proximity to the outer tube 2 as shown. The electrodes 5 are coextensive with the length of the excitation section 4.

A ring-shaped full reflecting mirror 8 is provided in and sealed to the annular space 3 between the inner and outer tubes 1 and 2 at an end of the excitation section 4 which, as depicted, is coplaner with the ends of the inner and outer tubes 1 and 2. The full mirror 8 is configured in a known manner to reflect radiation into the annular space 3.

A ring-shaped output resonator mirror 9 is provided in and sealed to the annular space 3 at the opposite end of the excitation section 4. A lasing gas such as $CO_2$ is provided in the annular space 3 between opposed mirrors 8 and 9.

It is noted that while FIG. 1 (and FIG. 4) depicts the excitation section 4 as extending from one end of the inner and outer tubes 1 and 2, it is possible to have the inner and outer tubes 1 and 2 extend beyond either end of the excitation section 4. The excitation section 4 is actually defined between the electrodes 6 and the opposed mirrors 8 and 9. Extending the inner and outer tubes 1 and 2 beyond the full reflecting mirror 8, will provide portions of the tubes at which an annular support(s) can be included to maintain the relative position and alignment of the tubes. In order to simplify the figures, supports between the tubes and electrodes are not shown. It is to be understood that supports used in the present invention can include any of a variety of known support structures which are conventionally used in various known coaxial tubular devices. One simple manner of maintaining the flexible coaxial alignment is to extrude an alignment bead or beads onto one or the other tubing surfaces which will maintain the spacing yet allow small movement necessary for flexibility. Since the sapphire fibers are extruded through a die, a suitable die which produces such beads can easily be provided.

FIG. 2 is a schematic diagram of a cross sectional view of the laser delivery device of FIG. 1 taken along line II—II. The preferred cross sectional shape of electrodes 6 can be seen in FIG. 2. The arcuate inner portions of the electrodes have a diameter which is slightly larger than the outer diameter of the outer tube 2 as depicted so that the electrodes 6 can be positioned adjacent to the outer tube 2 to concentrate rf energy toward the annular space 3. The length of a cord extending between the end points of the arcuate portion 7 of the electrodes 6 is preferably greater that the inner diameter of the outer tube 1 as depicted in FIG. 2. This ensures that rf energy generated between the electrodes 6 passes through the entire cross sectional area of the annular space 3 so as to maximize the rf pumping.

In operation, a conventional means for applying rf power is connected to electrodes to establish a discharge in the gaseous medium provided in the annular space 3 of the excitation section 4. The gaseous medium, i.e., the lasing gas, according to a preferred embodiment is $CO_2$ (10.6 $\mu$m). In further embodiments various other conventional lasing gases capable of lasing in the 8–14 $\mu$m spectral region can be excited and propagated in the co-axial system.

As a result of the discharge created in the gaseous medium provided in the annular space 3 of the excitation section 4, optical laser radiation is established in the annular space 3 of the excitation section 4 between the full reflecting mirror 8 and the output resonator mirror 9. Resulting laser radiation passes through output resonator mirror 9 and is guided during propagation through the annular space 3 and out the delivery end 10 of the laser delivery device.

Figure 3:
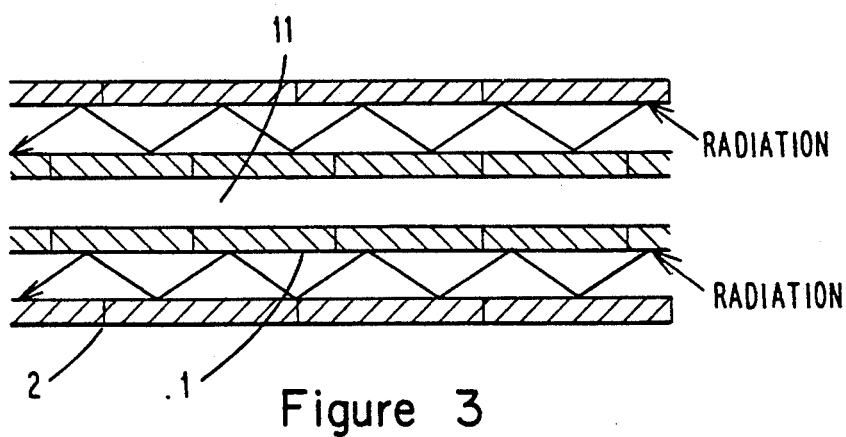
FIG. 3 is a schematic diagram of a cross sectional view of the radiation propagation and delivery section of the device of FIG. 1 which depicts the manner in which radiation is propagated and delivered therefrom.

FIG. 3 is a schematic diagram of a cross sectional view of the radiation propagation and delivery section of the device of FIG. 1 which depicts the manner in which radiation is propagated and delivered therefrom. As depicted in FIG. 3, laser radiation, which is generated in the excitation section 4, is internally reflected within the annular space 3 of the radiation propagation and delivery section 5 as it passes therethrough. In order to achieve this internal reflection, the inner and outer tubes 1 and 2 are made from a material such as sapphire which is known to reflect the radiation. Other known reflective materials can also be used. In addition, it is possible to coat or clad the inner surface of the outer tube 2 and the outer surface of the inner tube 1 with a reflective material to achieve the necessary reflectance. Any known cladding material, (e.g. Au, or multi-layer coatings) which reflects radiation can be utilized for this purpose.

The laser delivery device depicted in FIGS. 1-3 includes two coaxial hollow tubes. This embodiment provides for a central passage 11 which can be utilized in a number of ways. For example, a guide wire can be placed in the central passage 11 and used to position the device within a tubular lumen in a manner similar to a catheter. In addition, an optical viewing fiber or ultrasonic transducer can be inserted into central passage 11 and used for observation purposes during a laser procedure. In other procedures, the central passage 11 can be used to remove material, by suction, and/or deliver material such as flushing or cooling fluids, drugs, etc.

In the embodiment of the invention depicted in FIGS. 1-3 the radiation propagation and delivery section 5 can be of any suitable length to reach a remote situs, i.e., body lumen or cavity, to which laser radiation is to be applied. In addition, the inner and outer tubes 1 and 2 can be made of a flexible material which will assist in manipulation of the laser delivery section for positioning purposes. Moreover, to ensure alignment of the inner and outer tubes, thin support structures, i.e., webs joining the inner and outer tubes, could be provided which extend length-wise in the annular space 3. Another method is to entrude centering beads onto one of the tubing surfaces as discussed above.

Figure 4:
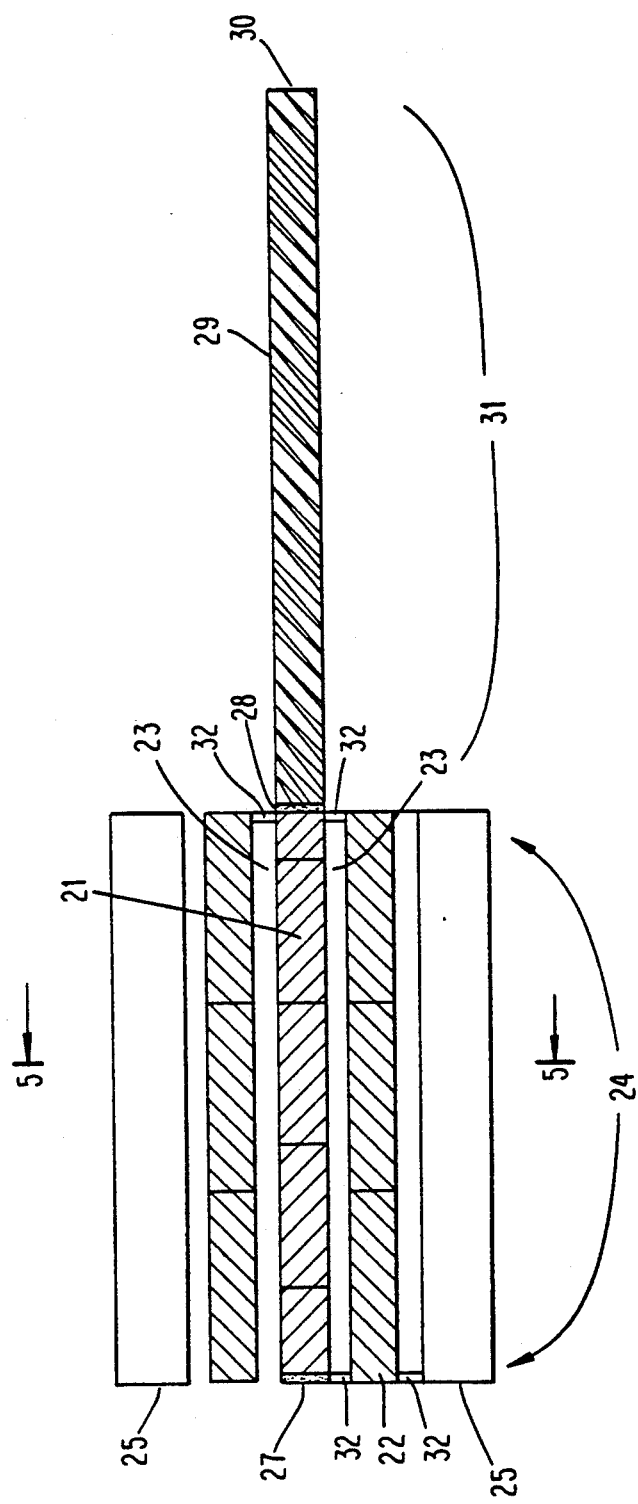
FIG. 4 is a schematic diagram of a cross sectional view of a laser delivery device according to another embodiment of the present invention.

FIG. 4 is a schematic diagram of a cross sectional view of a laser delivery device according to another embodiment of the present invention. The laser delivery device of FIG. 4 is made from two coaxial tubes, including solid inner tube 21 and a hollow outer tube 22. An annular space 23 is defined between the inner tube 21 and the outer tube 22. As discussed hereafter, in this embodiment, a pumping gags provided in the annular space 23 is excited by rf power and radiation from the pumping gas is transferred into the inner tube 21 in which lasing occurs. Radiation propagation and delivery are conducted within an extension of the inner tube 21 which, as discussed below, can be either solid or hollow.

Figure 5:
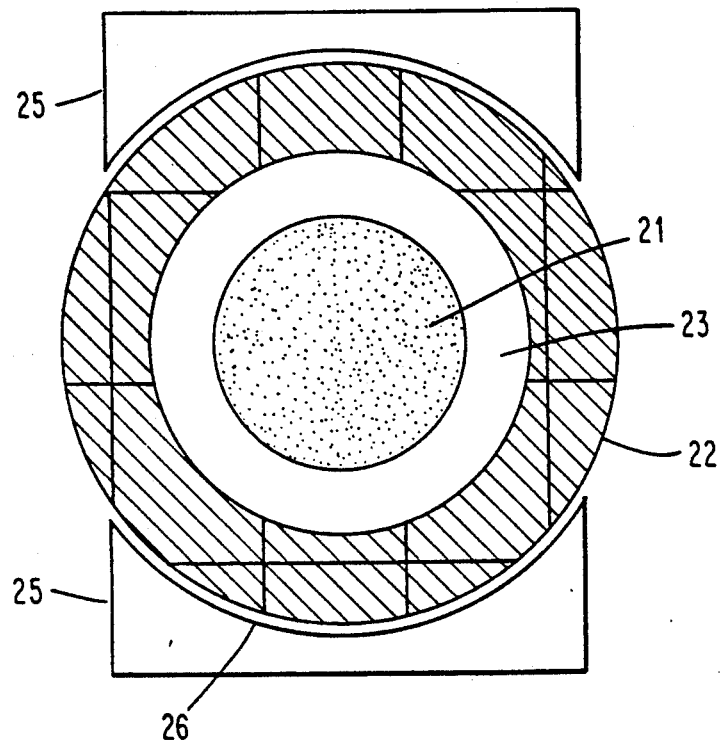
FIG. 5 is a schematic diagram of a cross sectional view of the laser delivery device of FIG. 4 taken along line IV—IV.

As depicted in FIG. 4, the inner and outer tubes 21 and 22 are coextensive in length. A excitation section 24 in which lasing occurs extends the length of the inner and outer tubes. The excitation section 24 includes opposed electrodes 25 which have arcuate inner surfaces 26 (FIG. 5). The electrodes 25 are positioned in close proximity to the outer tube 22.

The electrodes 25 are preferably coextensive with the length of the excitation section 24. A full reflecting mirror 27 is provided on one end of the inner tube. The full reflecting mirror 27 comprises a reflective coating which is applied to the inner tube 21 in a known manner and is provided to reflect radiation into the inner tube. An output resonator mirror 28 is provided on the opposite end of the inner tube 21 or an adjustable mirror external from the tube and can be used. The output resonator mirror 28 comprises a semi-reflective coating which is also applied to the inner tube 21 in a known manner such as simple vapor deposition.

An annular space 23 is provided between the inner and outer tubes 21 and 22. During operation, as discussed below, a pumping gas is supplied in the annular space 23 between the inner and outer tubes 21 and 22. Sealing windows 32 contain the pumping gas.

A radiation propagation and delivery tube (fiber) 29 is attached or in very close proximity to the inner tube 21 at the output resonator mirror 28. The radiation propagation and delivery tube 29 can either be a solid tube with a cladding layer thereon or a hollow tube. In alternative embodiments both tubes 21 and 29 can be hollow.

FIG. 5 is a schematic diagram of a cross sectional view of the laser delivery device of FIG. 4 taken along line IV—IV. The preferred cross sectional shape of electrodes 25 can be seen in FIG. 5. The arcuate inner portions of the electrodes have a diameter which is slightly larger than the outer diameter of the outer tube 22 as depicted so that the electrodes 25 can be positioned adjacent to the outer tube 22 to concentrate rf energy toward the annular space 23. The length of a cord extending between the end points of the arcuate portions 26 of the electrodes 25 is preferably greater that the inner diameter of the outer tube 22 as depicted in FIG. 5. This ensures that rf energy generated between the electrodes 25 passes through the entire cross sectional area of the annular space 23 so as to maximize the rf pumping.

In operation, a conventional means for applying rf power is connected to electrodes to establish a discharge in the gaseous medium provided in the annular space 23 of the excitation section 24. In a preferred embodiment the pumping gas is $F_2$. In other embodiments pumping gases such as Xe, Kr, $H_2$, etc. or mixtures of gases such as Ne, Xe, and $NF_3$, and the like which are disclosed in U.S. Pat. No. 4,513,242 to Waynant et al, the disclosure of which is expressly incorporated herein by reference, can be used.

As a result of the discharge in the gaseous medium provided in the annular space 23 of the excitation section 24, radiation is pumped in to the inner tube 21 which is doped with a lasing medium such as Nd in $LaF_3$ or more conventional dopants in more conventional hosts. Optical feedback or resonance is established in the inner tube 21 between the full reflecting mirror 27 and the output resonator mirror 28. Resulting laser radiation passes through output resonator mirror 28 and is guided during propagation through radiation propagation and delivery tube 29 and out the delivery end 30 thereof.

Figure 6:
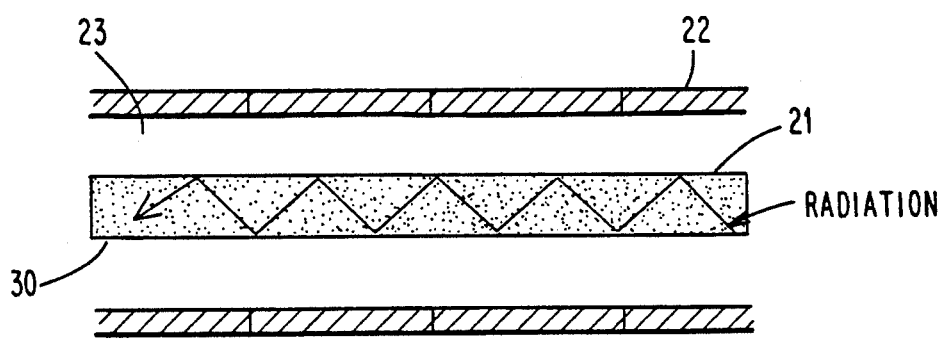
FIG. 6 is a schematic diagram of a cross sectional view of the radiation propagation and delivery section of the device of FIG. 4 which depicts the manner in which radiation is propagated and delivered therefrom.

FIG. 6 is a schematic diagram of a cross sectional view of the radiation propagation and delivery section of the device of FIG. 4 which depicts the manner in which radiation is propagated and delivered therefrom. As depicted in FIG. 6, laser radiation, which is generated in the excitation section 24, is internally reflected within tube 29 of the radiation propagation and delivery section 31 as it passes therethrough. In order to achieve this internal reflection, a cladding layer is applied to the outer surface of radiation propagation and delivery tube 29. Any known cladding material which effects internal reflection can be utilized for this purpose.

In embodiments in which a hollow tube is used for the radiation propagation and delivery tube 29, the laser radiation can be internally reflected off the inner and outer surface of the hollow tube. To accomplish this, the hollow tube can be made from known materials which reflects the laser radiation, e.g., $LaF_3$ silica, sapphire or other material. In addition, it is possible to clad the inner and outer surface of the hollow tube to achieve the necessary reflectance. Any known cladding material which causes such reflection (i.e. of refractive index less than the tube,) can be utilized for this purpose.

The laser delivery device depicted in FIGS. 4–6 includes a single radiation propagation and delivery tube 29 to deliver laser radiation to a remote situs, i.e., body lumen or cavity, to which laser radiation is to be applied. To make the device more useful, the radiation propagation and delivery tube 29 can be made of a flexible material which will assist in manipulation of the laser delivery section for positioning purposes.

An additional embodiment in which no excitation is generated in Section 24, but in which a hollow tube doped for lasing 21 and an outer fiber 22 are extended to replace 29. In this embodiment an external laser can be propagated between 21 and 22 to pump 21 making 21 a laser fiber. This externally pumped hollow fiber laser can be directed for medical operation and also offer the hollow fiber benefits of the first-discussed embodiment.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. A laser delivery device comprising an excitation section and a radiation propagation and delivery section, wherein said excitation section includes:
    an inner tube;
    an outer tube surrounding said inner tube end being coaxial along the entire length therewith;
    an annular space defined between said inner and outer tubes and containing a gas;
    a resonator means; and
    means to apply a radio frequency discharge via coaxial electrodes in said excitation section to excite said gas in said annular space; and
    said radiation propagation and delivery section includes an extension of said inner tube which extends beyond said excitation section.

2. A laser delivery device according to claim 1, wherein said inner tube comprises a solid tube.

3. A laser delivery device according to claim 2, wherein said extension of said inner tube comprises a solid tube.

4. A laser delivery device according to claim 3, wherein said extension of said inner tube includes a cladding layer.

5. A laser delivery device according to claim 2 wherein said extension of said inner tube comprises a hollow tube.

6. A laser delivery device according to claim 5, wherein said extension of said inner tube comprises a material which causes internal reflection and propagation of radiation therein.

7. A laser delivery device according to claim 6, wherein said extension of said inner tube comprises sapphire.

8. A laser delivery device according to claim 5, wherein said inner tube and said extension thereof include an open central passageway which extends therethrough for passing materials therethrough.

9. A laser delivery device according to claim 1, wherein said inner tube comprises a hollow tube and said radiation propagation and delivery section further comprises an extension of said outer tube which is coextensive in length with said extension of said inner tube.

10. A laser delivery device according to claim 9, wherein said inner tube, said outer tubes and said extensions thereof each comprise a material which causes internal reflection and propagation of radiation within said annular space.

11. A laser delivery device according to claim 10, wherein said inner tube, said outer tubes and said extensions thereof are each made from sapphire.

12. A laser delivery device according to claim 1, wherein said means to apply a radio frequency discharge comprises a pair of electrodes which are coextensive with said excitation section and coaxial with said inner and outer tubes.

13. A laser delivery device according to claim 12, wherein said electrodes include arcuate inner surfaces.

14. A laser delivery device according to claim 1, wherein the gas in said annular space comprises carbon dioxide.

15. A laser delivery device according to claim 1, wherein said radiation propagation and delivery section includes an extension of said outer tube which extends beyond said excitation section.

16. A method of delivering laser radiation to a target area which comprises:
    providing concentric inner and outer tubes having an annular space defined therebetween which annular space contains a gas;
    applying a radio frequency discharge via coaxial electrodes to excite said gas in said annular space to generate using at least a portion of said inner tube to propagate and deliver said laser radiation from an end thereof to a target area.

17. A method of delivering laser radiation to a target area according to claim 16, wherein said inner tube is hollow.

18. A method of delivering laser radiation to a target area according to claim 16, wherein said inner tube includes a central passageway therethrough and said method further comprises passing a material through said passageway.

19. A method of delivering laser radiation to a target area according to claim 16, wherein said inner tube is solid.

20. A method of delivering laser radiation to a target area according to claim 16, wherein said target area is located within a living subject.

* * * * *